United States Patent [19]

Fuchs et al.

[11] 4,360,461
[45] Nov. 23, 1982

[54] PROCESS FOR OBTAINING CAPROLACTAM BY CLEAVING CAPROLACTAM OLIGOMERS

[75] Inventors: Hugo Fuchs; Elmar Frommer; Otto-Alfred Grosskinsky, all of Ludwigshafen, Fed. Rep. of Germany

[73] Assignee: BASF Aktiengesellschaft, Fed. Rep. of Germany

[21] Appl. No.: 287,696

[22] Filed: Jul. 28, 1981

[30] Foreign Application Priority Data

Aug. 14, 1980 [DE] Fed. Rep. of Germany ....... 3030735

[51] Int. Cl.$^3$ ............................................ C07D 201/12
[52] U.S. Cl. ................................................ 260/239.3 A
[58] Field of Search ................................. 260/239.3 A

[56] References Cited

U.S. PATENT DOCUMENTS

| | | | |
|---|---|---|---|
| 3,264,060 | 8/1966 | Nieswandt et al. | 260/239.3 A |
| 3,350,393 | 10/1967 | Petri et al. | 260/239.3 A |
| 3,939,153 | 2/1976 | Fowler | 260/239.3 |

FOREIGN PATENT DOCUMENTS

819683 9/1959 United Kingdom .

OTHER PUBLICATIONS

Ullmanns Encyklopädie der technischen Chemie, 4th Edition, vol. 9, p. 100.
Chemical Abstracts, vol. 84, 1976, No. 17764j.
Chemical Abstracts, vol. 63, No. 5, 1965, Spalte 5833e.
Chemical Abstracts, vol. 88, 1978, No. 170762j.
Soviet Inventions Illustrated, Section Chemical, Derwent Publications, Ltd., Jul. 1966, Section 1, p. 13.

*Primary Examiner*—Robert T. Bond
*Attorney, Agent, or Firm*—Keil & Witherspoon

[57] ABSTRACT

In a process for obtaining caprolactam by cleaving caprolactam oligomers by passing them through an alumina catalyst bed at an elevated temperature, the improvement that the oligomers are introduced, as liquid or solid, into a fluidized bed of alumina and are cleaved at from 290° to 400° C. in the presence of steam.

5 Claims, No Drawings

PROCESS FOR OBTAINING CAPROLACTAM BY CLEAVING CAPROLACTAM OLIGOMERS

The preparation of caprolactam results in the first instance in polycaprolactam containing about 10% of monomers and oligomers. The monomers and oligomers are extracted from the monomer-containing polycaprolactam by conventional methods, using water. The water is evaporated and the extracted caprolactam recovered. However, substantial amounts of oligomers remain, and these require appropriate treatment.

German Pat. No. 950,726 discloses a process for cleaving polycaprolactam to give its monomer, wherein polycaprolactam is heated with an acid, such as phosphoric acid, in the presence of water. However, to obtain high quality caprolactam it is necessary to treat the caprolactam obtained with an oxidizing agent. This, however, is very expensive if carried out industrially. According to British Pat. No. 819,683, caprolactam oligomers are cleaved by passing the oligomer vapor, at 400° C., over a bed of inert materials, such as sand or silicates. However, the yield achieved is only 66%. According to the process disclosed in U.S.S.R. Pat. No. 176,680, caprolactam oligomers are passed as vapor, at 250°-260° C., through an alumina catalyst bed. This process can be utilized without difficulty only if the monomeric lactam and the oligomers are removed from the polymer by thin film evaporation or similar methods and accordingly are in any case in vapor form. The caprolactam obtained furthermore has a high permanganate titer and high ultraviolet number (see later), so that it cannot be worked up conjointly with ordinary crude caprolactam without substantially lowering the quality of the latter. Accordingly, it is necessary separately to purify the caprolactam obtained as described above, and this is very expensive in industrial operation.

It is an object of the present invention to provide a method of cleaving caprolactam oligomers which gives high yields and provides caprolactam of a quality such that the material can be worked up, without disadvantage, conjointly with ordinary crude caprolactam.

We have found that this object is achieved by a process for obtaining caprolactam by cleaving caprolactam oligomers by passing them through an alumina catalyst bed at an elevated temperature, wherein the oligomers are introduced, as liquid or solid, into a fluidized bed of alumina and are cleaved at from 290° to 400° C. in the presence of steam.

The novel process has the advantage that it gives high yields and that the caprolactam obtained has a lower permanganate titer and ultraviolet number. It has the further advantages that the oligomers do not have to be vaporized in a separate step before cleavage, and that the caprolactam obtained can be worked up together with ordinary crude caprolactam, without lowering the quality of the latter.

Oligomers employed as starting materials as a rule have a degree of polymerization, n, of from 2 to 9. In particular, such materials contain dimeric and trimeric cyclic oligomers. Such oligomers are obtained, for example, by evaporating the wash waters resulting from the extraction of polycaprolactam, and then removing monomeric caprolactam from the evaporation residue by distillation. Advantageously, the oligomers are employed as a mixture with caprolactam, and accordingly it is not necessary to distil off all the caprolactam from the said extract. Suitable mixtures contain, for example, from 10 to 60% by weight of oligomers and from 90 to 40% by weight of caprolactam. The oligomers or mixtures of oligomers and caprolactam are advantageously introduced as a liquid, i.e. in the molten state, for example at from 150° to 250° C., into a fluidized bed of alumina. However, it is also possible to introduce the oligomer, or the oligomer/lactam mixture, in a finely divided solid form into the fluidized bed and to cleave it catalytically therein, to give monomeric caprolactam. The material is introduced into the fluidized bed by, for example, blowing it in by means of a nozzle, with an inert gas propellant. Alumina in various modifications, such as alumina and boehmite, can be used as the catalyst, but $\gamma$-alumina has proved particularly suitable. The catalyst is fluidized by means of an inert gas, such as carbon dioxide, argon or nitrogen, the last-mentioned being preferred. Advantageously, the alumina has a particle size of from 0.05 to 1.5 mm, especially from 0.2 to 1 mm. The height of the catalyst bed is advantageously such that the residence time of the oligomer in the bed is from 0.1 to 30, especially from 0.5 to 10, sec. The process is advantageously carried out under atmospheric pressure but can also be carried out under slightly reduced or slightly superatmospheric pressure, for example at up to 2 bar.

The catalyst bed is kept at from 290° to 400° C., especially from 300° to 360° C. It is therefore also advantageous if the inert gas fed to the fluidized bed is at from 290° to 400° C.

According to the invention, the cleavage is carried out in the presence of steam. Advantageously, 0.005–10 parts by weight, especially 0.02–2 parts by weight, of water in the form of steam are used per part by weight of oligomer. The water to be used can be introduced as such into the fluidized bed, and vaporized therein. Preferably, however, the water is introduced in the form of steam which can also, for example, be introduced into the fluidized bed conjointly with the inert gas.

The gas mixture leaving the fluidized bed is condensed in a bubble-cap tray column, by charging water to the top of the column, as described, for example, in German Published Application DAS No. 1,445,549. The bottom product obtained is caprolactam, whilst inert gas and steam leave the top of the column. The steam can be condensed out of the inert gas and the inert gas can advantageously be recycled to the fluidized bed.

The condensed caprolactam can be additionally purified, for example by distillation, and the caprolactam thus recovered can then be added to caprolactam which has been obtained from a Beckmann rearrangement and requires purification, the materials then being worked up conjointly, for example as described in German Patent 1,194,863 or in Ullmanns Encyklopädie der technischen Chemie, 4th Edition, Volume 9, page 100.

It is however also possible to condense the caprolactam out of the vapor mixture leaving the reactor, as described above, add this direct to the crude lactam from the Beckmann rearrangement, and work up the materials conjointly.

Caprolactam is used for the preparation of polycaprolactam. The Examples which follow illustrate the process according to the invention.

To determine the volatile bases, 40 ml of 30% strength sodium hydroxide solution, followed by a solution of 20 g of substance in 80 ml of distilled water, are introduced into a Kjeldahl apparatus, and rinsed in with 20 ml of distilled water. Thereafter, steam is blown into the apparatus and 50 ml of water are distilled, in the course of 5 minutes, into a receiver which contains 5 ml of N/50 hydrochloric acid, 30 ml of water and 5 drops of indicator solution. The condenser and exit tube are then rinsed out with distilled water into the receiver, and the unconsumed acid is back-titrated with N/50 sodium hydroxide solution. The amount of N/hydrochloric acid consumed, with due correction for the blank value, directly gives the amount of volatile bases in milliequivalents of base per kg of substance.

The permanganate titer is the consumption of N/10 potassium permanganate solution, in milliliters, when titrating a solution of 1.000 g of substance in 2.500 g of 50% strength aqueous sulfuric acid at room temperature until the permanganate color persists for 2 minutes.

The permanganate absorption number is the extinction obtained by measuring the light transmission of a 1 percent strength caprolactam solution in water (50 ml or 100 ml being used) after adding respectively 1 or 2 ml of 0.01 $KMnO_4$ solution and leaving to stand for 600 sec. at 25° C., the measurement being made at 420 nm against an identical solution without caprolactam.

The ultraviolet number is obtained, in principle, by measuring the absorption of the caprolactam in the spectral range of 360–270 nm and expressing the appropriately converted measurement as a characteristic number. The equipment used comprises a recording single-beam spectrophotometer, a 200 ml Erlenmeyer flask and 2 quartz cells with covers, the cells being 10 cm long, ie. providing a 10 cm thickness of solution.

50 g of caprolactam are dissolved in 50 g of cold doubly-distilled water in an Erlenmeyer flask. One cell is filled with this solution up to the calibration mark. The second cell is filled with the same doubly-distilled water and constitutes the comparative solution. Both cells are closed with their lids, the ground faces are cleaned with tissue paper and the cells are inserted in the holders. The spectrum is then recorded between 370 nm and 260 nm, in accordance with the apparatus instructions, at a recording speed of 50 and using the 0–1 scale range for the extinction measurement.

When the recording has been completed, marks are made on the paper at intervals of 10 nm between 270 and 360 nm. The extinctions are read off the diagram at 270, 280, 290, 300, 310, 320, 330, 340, 350 and 360 nm and summed. The sums of the 10 extinctions is multiplied by 2 and gives the UV number. This number accordingly always relates to 100% strength caprolactam and to a 10 cm thick layers.

EXAMPLE 1

1,000 g of catalyst, consisting of γ-alumina, which has been calcined at 800° C. and has a particle size of from 0.2 to 0.8 mm, are heated to 320° C. in a vertical, insulated, electrically heated tube, having a length of 1,200 mm and a diameter of 100 mm, and provided with a perforated plate at the bottom. The catalyst is fluidized by a stream of nitrogen, of 2,500 liters (S.T.P.)/h, which is pre-heated to 360° C. and blown in through the perforated plate. In the course of one hour, 4,500 g of a caprolactam oligomer melt, containing 30% of oligomers, taken from a stock vessel at 170° C., is injected into the catalyst bed, by means of a stream of nitrogen of 1,500 liters (S.T.P.)/h, which has been preheated to 200° C., through an upward-pointing two-material nozzle located centrally in the tube, 90 mm above the perforated plate. 600 g per hour of steam are added to the preheated stream of nitrogen. The catalyst bed is kept at 320° C. by electrical heating. The vapors leaving the reactor are condensed in a column of 100 mm diameter, equipped with 10 bubble-cap trays, by charging water to the top of the column. Per hour, 4,320 g of caprolactam free from oligomers are obtained. The product has the following characteristics (based on anhydrous lactam): permanganate titer 180, ultraviolet number 520.

500 g of this lactam are added to 5,000 g of lactam having a permanganate titer of 50 and an ultraviolet number of 110, and containing 0.6 milli-equivalent of volatile bases/kg, and the materials are worked up conjointly by distillation under reduced pressure, to give pure lactam.

The pure lactam obtained has the following properties:

Solidification point: 69.1° C.
Permanganate titer: 1.7
Permanganate absorption number: 3.6
Ultraviolet number: 4.8
Extinction at 290 nm of a 1 cm layer of 50% strength aqueous solution: 0.03
Volatile bases: 0.15 milliequivalent/kg

COMPARATIVE EXAMPLE 1

Using the method described in Example 1, 4,500 g per hour of a caprolactam oligomer melt containing 30% of oligomers are injected, at 170° C., without addition of steam, into the reactor. The catalyst used is γ-alumina which is fluidized with 2,500 liters (S.T.P.)/h of nitrogen which has been pre-heated to 360° C. The vapor mixture leaving the reactor is condensed in a bubble-cap tray column, as described above. 4,280 g of caprolactam having the following properties are obtained: permanganate titer 1,000, ultraviolet number 1,500.

The analytical data of the lactam obtained by cleavage are thus substantially less good than those in Example 1.

COMPARATIVE EXAMPLE 2

200 g of caprolactam oligomers are introduced into a flask equipped with thermometer, gas outlet tube and gas inlet tube. The oligomers used are obtained from the aqueous extract from nylon production; the water is removed from the extract and the lactam then distilled off, leaving the oligomers as the residue.

After addition of 5% of $H_3PO_4$, the contents of the flask are heated, under atmospheric pressure, to 340° C. by means of a molten metal bath. At the same time, about 200 g of water is vaporized, pre-heated to 340° C. and passed through the melt. The vapor mixture issuing from the flask is condensed and analyzed.

175 g of caprolactam are obtained, having the following properties: permanganate titer 2,500, ultraviolet number 7,500.

This lactam is added, in an amount of 1.5% of 100% strength material, to an extract lactam having a permanganate titer of 50 and an ultraviolet number of 110, and containing 0.6 milliequivalent of volatile bases/kg. The mixture is then worked up by distillation, as described.

The pure lactam has the following properties:
Permanganate titer: 6.0
Permanganate absorption number: 8.5
Ultraviolet number: 15
Extinction at 290 nm of a 1 cm thick layer: 0.16
Solidification point: 69.0° C.
Volatile bases: 0.48 milliequivalent/kg This lactam lies outside the conventional sales specification.

EXAMPLE 2

1,000 g of γ-alumina catalyst are heated to 320° C. in an apparatus as described in Example 1, and fluidized with 2,500 liters (S.T.P.)/h of nitrogen. 400 g per hour of oligomers in powder form are introduced into the hot catalyst bed through a nozzle operated with about 2,000 liters (S.T.P.)/h of nitrogen. Simultaneously with the nitrogen required for fluidizing, 2,000 g of steam are introduced into the catalyst bed. The vapor mixture leaving the reactor is condensed as has been described above.

360 g per hour of monomeric caprolactam are obtained having the following properties: permanganate titer 300, ultraviolet number 400.

250 g of this lactam together with 2,500 g of extract lactam are worked up as described above to give pure lactam. The latter has the following properties:
Solidification point: 69.12° C.
Permanganate titer: 1.4
Permanganate absorption: 4.2
Ultraviolet number: 3.55
Extinction of a 1 cm layer of 50% strength aqueous solution at 290 nm: 0.25
Volatile bases: 0.11 milliequivalent/kg If the procedure described in Example 2 is followed but no steam is introduced during cleavage, the input of 400 g of oligomers per hour results in 352 g of monomeric caprolactam having the following properties: permanganate titer 1,000, ultraviolet number 3,000.

Mixing this lactam with extract lactam in the same ratio as in Example 4, and then working up the mixture conjointly to give pure lactam, gives a product with properties lying outside the conventional sales specification.

We claim:

1. An improved process for obtaining caprolactam by cleaving caprolactam oligomers by passing them through an alumina catalyst bed at an elevated temperature, wherein the improvement comprises introducing the oligomers, as liquid or solid, into a fluidized bed of alumina and cleaving them at from 290° to 400° C. in the presence of steam.

2. A process as claimed in claim 1, wherein from 0.005 to 10 parts by weight of water, in the form of steam, are used per part by weight of oligomer.

3. A process as claimed in claim 1, wherein the cleavage is carried out at from 300° to 360° C.

4. A process as claimed in claim 1, wherein the oligomers are introduced conjointly with caprolactam into a fluidized bed of alumina.

5. A process as claimed in claim 1, wherein the catalyst used is γ-alumina.

* * * * *